United States Patent [19]

Burns et al.

[11] Patent Number: 5,419,200

[45] Date of Patent: May 30, 1995

[54] METHOD FOR ASSESSING THE EFFECTS OF LOADING FORCES ON A COMPOSITE MATERIAL STRUCTURE

[75] Inventors: Bruce P. Burns, Churchville, Md.; Travis A. Bogetti, Bear, Del.

[73] Assignee: The United States of America as represented by the Secretary of the Army, Washington, D.C.

[21] Appl. No.: 260,286

[22] Filed: Jun. 14, 1994

[51] Int. Cl.$^6$ ............................................. G01B 5/30
[52] U.S. Cl. ..................................... 73/760; 73/810; 73/789
[58] Field of Search ................. 73/762, 789, 794, 799, 73/760, 810, 818, 826, 150

[56] References Cited

U.S. PATENT DOCUMENTS

| | | | |
|---|---|---|---|
| 4,936,141 | 6/1990 | Anderson, Jr. et al. | 73/159 |
| 5,201,424 | 4/1993 | Hain | 73/159 |

OTHER PUBLICATIONS

Hahn et al., "Constitutive Modeling of Composite Laminates with Progressive Ply Cracking", Technical Report BRL-TR-3399, Sep. 1992.

*Primary Examiner*—Richard E. Chilcot, Jr.
*Assistant Examiner*—Max H. Noori
*Attorney, Agent, or Firm*—Freda L. Krosnick; Muzio B. Roberto; Charles H. Harris

[57] ABSTRACT

To determine the optimum load a laminate member or element is capable of bearing, a three-dimensional progressive analysis is proposed in which the stress and strain states of each ply of the laminate are subjected to failure criteria. If there is failure, new ply stiffness parameters are calculated. Thereafter, the ply is tested with the new parameter until the optimal load is determined. If no failure is detected for a given stress and strain for the ply then the load may be incremented and again applied to the ply, for further testing. Alternatively, the same load may be applied to the ply for a further period of time, until the optimal load is determined and/or the analysis is deemed to be finished.

11 Claims, 5 Drawing Sheets

INDIVIDUAL PLIES          LAMINATE

INDIVIDUAL PLIES　　　　　　LAMINATE

METHOD FOR ASSESSING THE EFFECTS OF LOADING FORCES ON A COMPOSITE MATERIAL STRUCTURE

FIELD OF THE INVENTION

The present invention relates to analysis of composite material structures and more particularly to the analysis of progressive structural damage of a composite material member such as a laminate or layered structure composed of multiple plies bonded together. More in particular, the present invention is directed to a computational methodology for multi-dimensional analysis of composite material structures.

DISCUSSION OF THE PRIOR ART

The analysis of continuous fiber reinforced composite material structures poses many challenges. Localized failure during loading may cause a redistribution of internal stress within a structure that does not necessarily lead to catastrophic failure. In fact, composite structures often undergo a series of complex progressive failure paths prior to catastrophic failure.

Existing, advanced computational methodologies used to structurally assess complex composite material structures are reasonably accurate at predicting the stress and strain states throughout a structure up to a load level where the first localized failure occurs. Such localized failure is generally not catastrophic for the entire structure. Initially, the localized failure will alter the anisotropic stiffness properties of the composite material in a small local region within the structure. Subsequently, a redistribution of the local stress and strain states occurs as the load path changes. The introduction of an incremental arbitrary load beyond the initial threshold of damage may or may not cause further progressive damage or could ultimately lead to gross structural failure if the incremental load is sufficiently large.

Presently, no computational methodology exists that would address the general logistics of progressive damage in arbitrary or complex shaped composite material structures or components. Rather, all analytical assessment techniques for complex composite material structures that are being practiced today are based on stress and strain state distributions that do not incorporate the effects associated with progressive damage and local load redistribution. Consequently, but for a small class of structurally simple and limiting cases, the current techniques are inadequate for ascertaining the ultimate failure loads.

BRIEF DESCRIPTION OF THE PRESENT INVENTION

The present invention computational method significantly enhances the current state of the art methodologies for assessing structure fabricated from continuous fiber reinforced composite materials. It allows for the estimation of effects due to local damage in the composite materials of the structure which are subjected to arbitrary, but sufficiently intense loads, which are often characterized by steep gradients in the stress and strain states. The present invention method is intended to function with numerical analyses such as the finite element or finite difference numerical methods to provide accurate estimates of ply level mechanical stress and strain states.

Whereas all known methods are restricted or limited to a particular set of load configurations, failure modes or structural geometries, the present invention method is entirely independent of such, and is therefore unique for failure assessment of laminate composite structures. The present invention method is moreover intended to provide the means for assessing ply degradation including all relevant factors. And by applying the loads incrementally, the present invention method allows assessment of progressive degradation of a composite material induced by localized and potentially propagating ply damage.

Briefly, to begin, element stiffness of the being assessed composite layered member is formulated in the present invention method. Thereafter, global displacements of the plies of the member are computed. The stress and strain states of the plies of the member are next deduced. Failure criteria are then applied to determine whether there is failure in each ply of the element. If there is, new ply stiffness parameters are computed and stored. Any change between the newly computed stiffness parameters and the previously stored stiffness parameters for the ply are determined. If the change is significant, the element stiffness is reformulated. If the change is insignificant, an increment of the load is further applied to the member. Alternatively, the same load may be applied for an additional time to the ply. This process continues until the analysis is finished or determination is made that there is significant failure in the ply. The present invention method therefore allows the accurate monitoring of any damage or failure to individual plies of the member. It further allows for monitoring the redistribution of the load through the member to regions of the different plies where failure has not occurred. Also, it allows for the measurement of the maximum load which a member can be subjected to before it fails.

It is therefore an objective and advantage of the present invention method to accurately monitor any damage and to adjust the relative or local contribution of individual plies of a composite element and the associated redistribution of internal stress and strain of the member.

It is moreover another objective and advantage of the present invention to provide a method that codifies automated procedures for shifting through voluminous amount of numerical data to provide interpretation of the stress and strain states of a laminated structure.

BRIEF DESCRIPTION OF THE DRAWINGS

The above mentioned objectives and advantages of the present invention will become more apparent and the invention itself will be best understood by reference to the following description of an embodiment of the invention taken in conjunction with the accompanying drawings, wherein.

DETAILED DESCRIPTION OF THE PRESENT INVENTION

Figure 1:
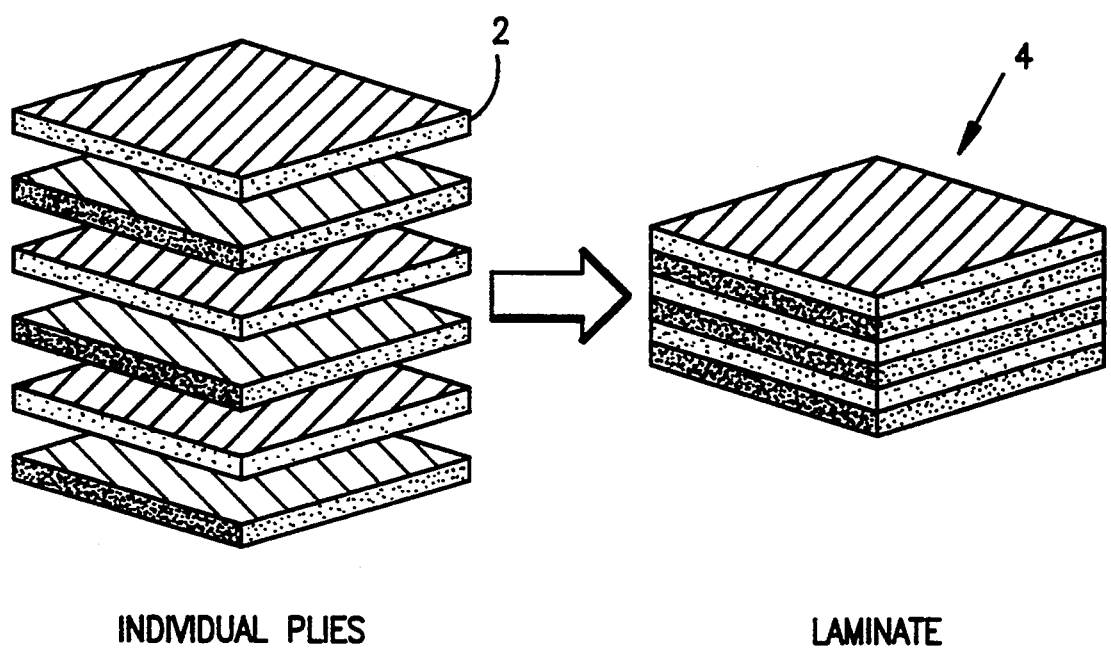
FIG. 1 is an illustration of a composite material laminate member or element comprising a number of individual plies each made up of fibers of either a polymeric or metal matrix material.

In order to ascertain local failure in continuous or long fiber-reinforced composites in complex structures with significantly large spatial gradients of stress and strain states, it is necessary to evaluate the failure at the ply level. Such localized failure may be included in any of several categories, broadly characterized as fiber failure, matrix failure, interlaminar (interply) failure or interactive failure each with corresponding levels of tensile, compressive and shear allowables, or interactive failure characteristics. Further, the achievable levels of strength parameters have some natural structural variation for perfectly made parts (for example one fiber in a tow (a bundle of fibers) is the weakest, one is strongest, and some distribution exists between the two for the rest of the fibers). Part quality if known to be a major factor in achieving strength, so that factors related to void content, excess matrix, fiber waviness, etc., have a great importance in failure determination.

The fundamental "continuum level" to which localized failure may be addressed is the ply level. Typically, individual plies of fiber-reinforced composite material or laminas are stacked or assembled into a laminate or layered member see FIG. 1. The laminate is the basic building block element or member of a composite structure. It is, therefore, necessary for a computational approach to capture the geometric details from a ply-by-ply description and generate appropriate element stiffness which represent the particular geometry contained within a particular element's coordinates or boundaries. It is also necessary to successfully describe the three-dimensional states of stress and strain for each ply contained within an element (to include variations of these states for each ply within an element caused by stress, strain, displacement, etc., gradients). Such computations are possible with varying degrees of generality by several approaches. Some focus on special pre- and post-processors, while others use specialized element formulations to treat plies bounded in part, by element boundaries defined by ply surfaces. Still others have focused on tractable, simple techniques to assess gradual, progressive failure in an analytical based fashion. See "Constitutive Modeling of Composite Laminates with Progressive Ply Cracking" by Hahn et al. Such approaches typically neglect three-dimensional effects and ignore stress and strain gradients which are inherent in realistic structures, especially in the vicinity of joints and geometric discontinuities.

Since most problems can be solved numerically with an incremental loading strategy, which is necessary in transient problems and for those involving non-linear material response, the framework exists to computationally assess localized failure (within a ply or otherwise), adjust the stiffness matrix describing the element in which such a failure has occurred, and use the information to either recompute the state of stress or strain at the current load increment (or time step) or for the next time or load step. Whether or not an intuitive procedure is adopted will depend on many factors such as numerical accuracy, how well the physical failure mechanisms can be represented as well as other related arguments. Several types of approaches or modeling methodologies are available. A first method would concentrate on the revision of ply properties due to localized failures, the regeneration of the element stiffness based upon the derived damage into appropriate linear anisotropic material constants, and the continuation of the computations to allow further local damage assessment. A second approach, using appropriate non-linear, anisotropic constitutive models to simulate element response may also be feasible.

The success of such computational strategies depends on the accuracy of the assessments of damage to generate current ply status. History of previous damage must also be available to construct appropriate damage models. An example of such a damage state are effects related to delamination, where compression loads normal to the delamination can be maintained, but where tension normal to the delamination is no longer possible. Shear performance (interlaminar) at a delamination site would also be influenced, resulting in no interlaminar shear capacity when compressive normal stresses are not present and shear capacity in the presence of compressive normal stress limited by friction slippage effects rather than polymer or bond shear stress allowables. The complete evaluation of ply depends not only on the assessment and history involving interlaminar damage, but also on in-plane damage to both fibers and matrix.

In general, the assessment methodologies for in-plane damage will also depend upon the current stress and strain state and the entire damage history. History effects in real time will be important to resolve rate sensitive failure modes in a ply (including interlaminar details). The factors influencing ply damage assessment include the current three-dimensional status of stress and strain, prior damage, and the definition of allowables to establish damage thresholds. The latter may be rate dependent or distribution functions which describe fiber to fiber variations in strength or describe the quality of the part. Statistical or deterministic relationships are therefore used to describe such quantities as void content, fiber straightness, etc. This means that graceful degradation of ply strengths and other such notions of failure may be accommodated by pertinent approaches. Once the relative amount of damage is estimated, the ply stiffness parameters can then be computed to allow for the effects of the estimate damage to be described in the element stiffness. Again, one might use the information to compute the state of the next load increment or to iterate the computation to calculate improved information pertaining to the element's dependent variables before proceeding with the next time step.

Given the above discussion, an embodiment of the present invention method is herein described with reference to FIGS. 1-5.

As shown in FIG. 1, a laminate or layered member 4 is comprised of a plurality of individual plies 2, also known as laminas. Such laminate may be considered as an element of a composite structure such as a composite tubing. Each lamina 2 is made of continuous fibers in either a polymeric or metal matrix material. Alternatively, it may be made of long discontinuous but preferentially oriented fibers in either a polymeric or metal matrix material. The problem with a lamina in any one direction is that it has enormous compression strength in the direction of the fibers. However, it ordinarily does not have sufficient compression strength along the transverse direction of the fibers. Consequently, to make a strong laminate, each lamina has to be oriented so that its fiber orientation is out of phase with its adjacent lamina(s). This is shown in FIG. 1 where the different plies have their respective fibers oriented at different coordinate directions. All of the different plies are bonded together to form laminate 4. Because the stress and strain properties for each ply of the laminate may be different, to determine the optimal load that a particular laminate, such as 4, can bear along its axes, the present invention utilized the method set forth in FIG. 2.

In particular, as shown, the element stiffness is formulated per block 6, by means of some conventional method such as for example the laminated plate theory, for obtaining the mechanical properties. A more advanced calculation would entail finite element representation in which the member is broken down and the stiffness is calculated. Some other more exotic approaches such as three-dimensional plate theories may also be used. Once the anisotropic coefficient stiffness properties are obtained, the global displacements of the laminate are obtained in block 8. Essentially this is a finite element number cruncher in which the stress and strain states of the different regions of the laminate are determined. Thereafter, the stress and strain states for the different regions for each ply are determined in block 10, by means of any of a number of commercially available programs such as for example Abacus, Ansys or Nastran. The operations involved in blocks 8 and 10 can also be referred to as the smearing-unsmearing methodology, as shown in blocks 12-20 of FIG. 3.

Figure 2:
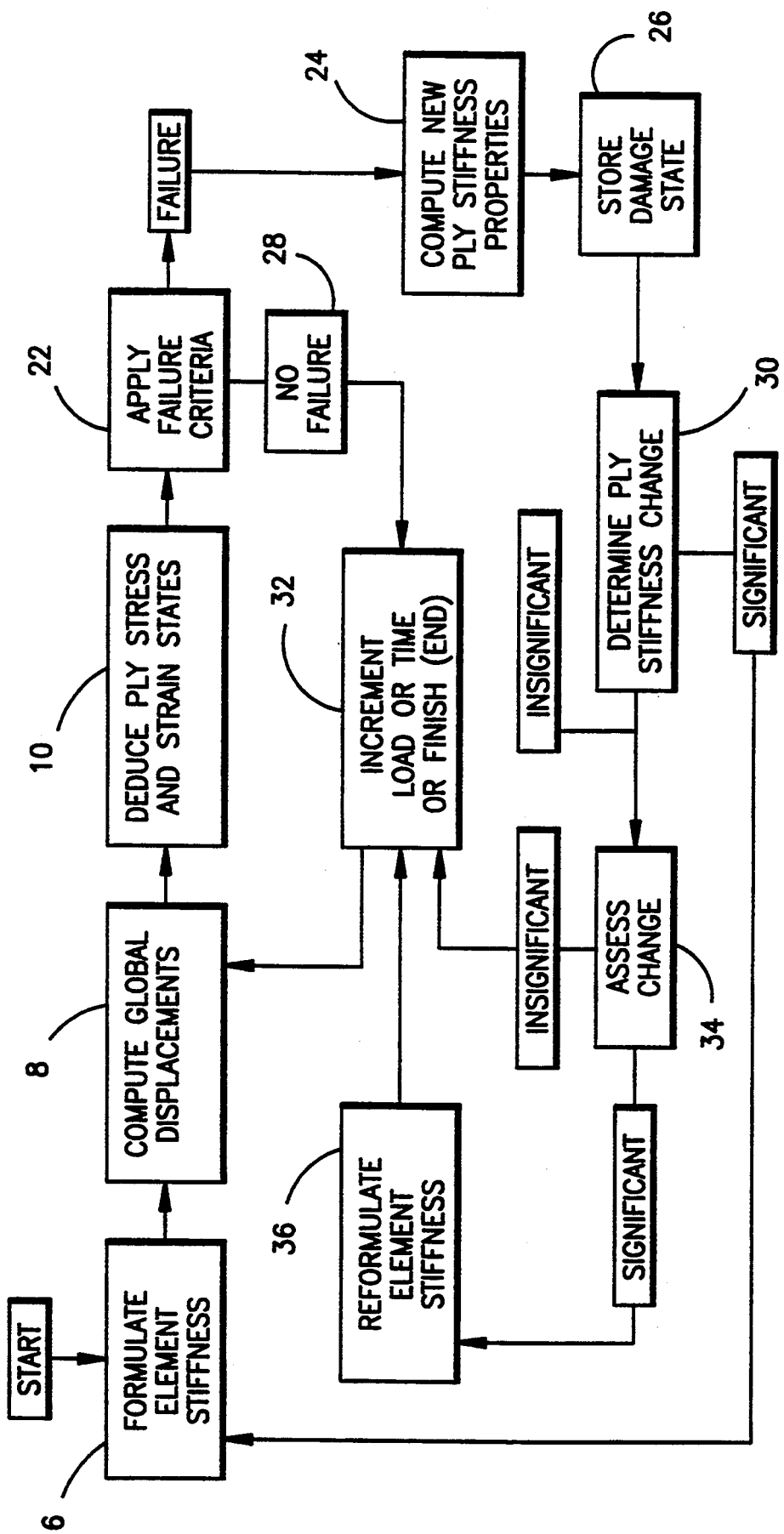
FIG. 2 is an illustration of a smearing-unsmearing methodology for formulating the element stiffness parameters of the FIG. 1 laminate member.
Figure 3:
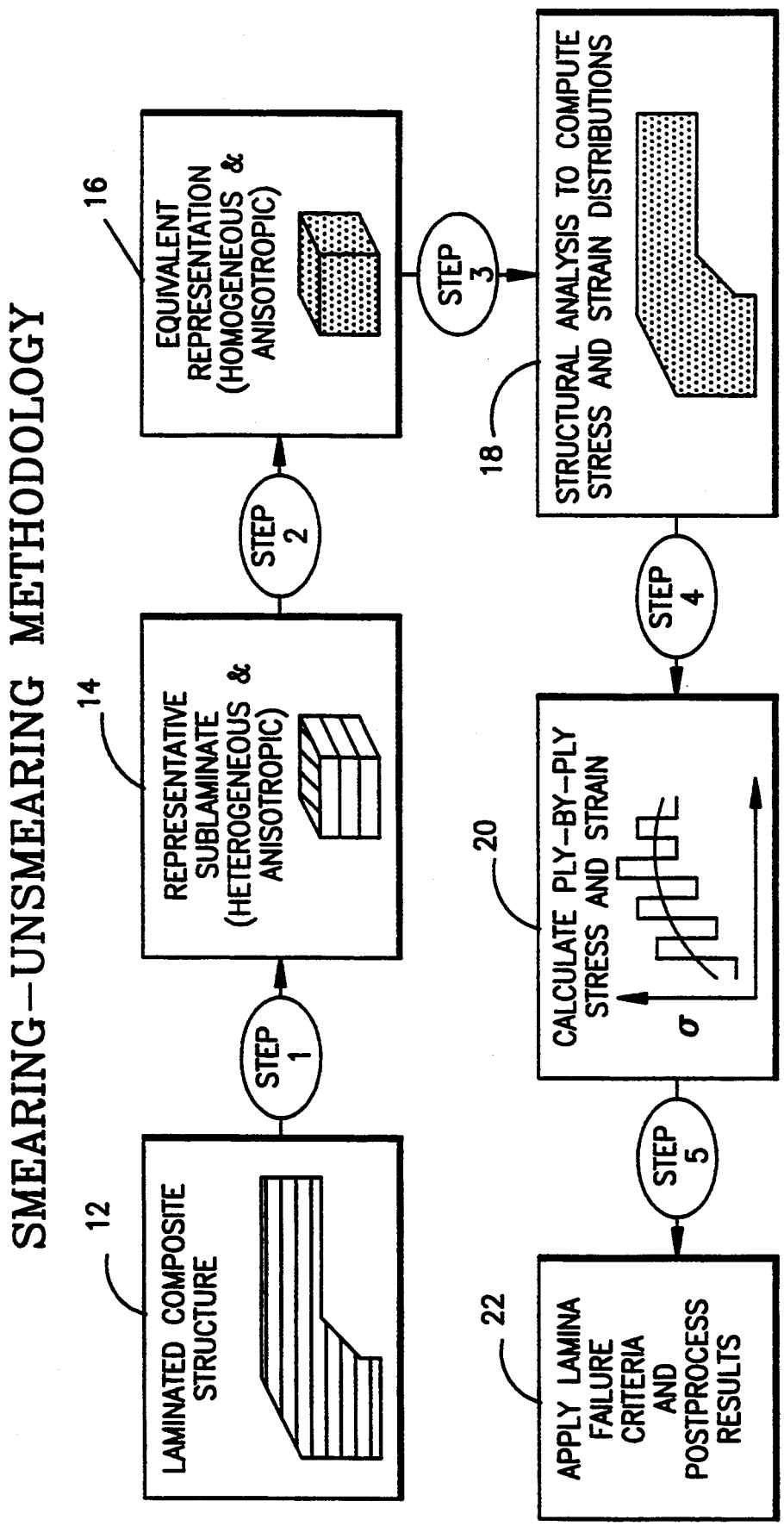
FIG. 3 is a block diagram of the method of the present invention.

After the stress and strain states for each ply of the laminate have been calculated, failure criteria are applied in block 22 (of both FIGS. 2 and 3). There are a variety of failure criteria. For the instant embodiment method, approximately 8 or 9 different types of failure criteria have been programmed. Essentially, these conventional failure criteria involve algebraic expressions of different components of stress and strain within a ply. A determination is then made on whether the being tested ply has passed or failed the different failure criteria. If it has failed, new stiffness parameters are computed for that ply per block 24. At the same time, the damaged information relating to the ply failure is stored per block 26.

Figure 4:
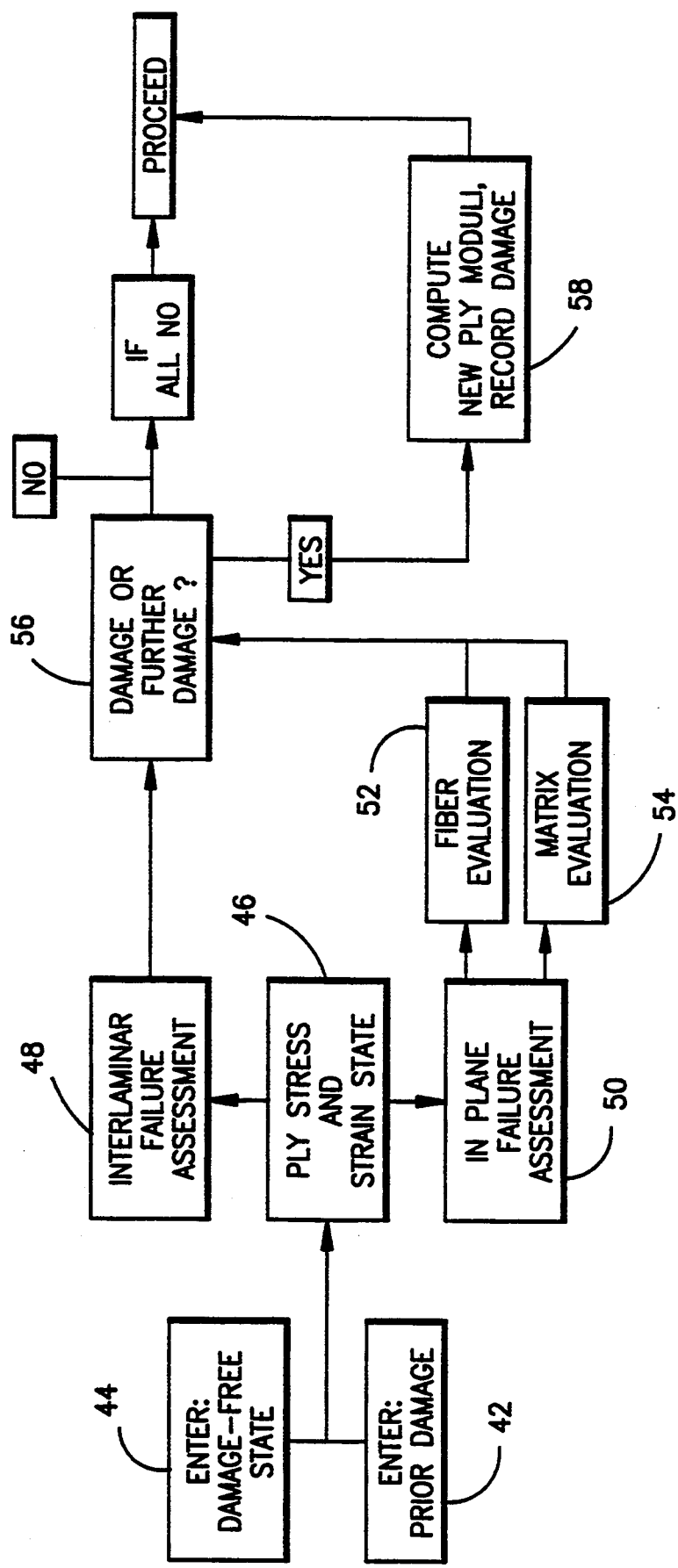
FIG. 4 is a flow chart block diagram illustrating in more detail certain blocks or steps in the FIG. 3 diagram.

With reference to FIG. 4, a more detailed flow chart illustrating the evaluation of ply damage is given. As shown, a first determination is made on whether the being tested ply has any prior damage or is one that is damage-free, per blocks 42 and 44, respectively, before loading forces are applied to the laminate. Prior damage in regard to the particular ply under test may be retrieved from a storage memory, provided that the damage state had previously been stored per block 26. The stress and strain states of the ply is next determined in block 46.

For the FIG. 4 illustration, two distinct modes of assessing failure due to stress and strain of the ply are provided. The first one is interlaminar failure assessment, per block 48, which may be considered as out of plane mode. An in-plane failure assessment, per block 50, is another mode for determining internal stress and strain of the ply. If it has been determined that it is in fact an in-plane failure for the ply, then further determination is made on whether the in-plane failure is to fiber failure, per block 52, or matrix failure, per block 54. Whether or not there is damage is then determined in block 56, which has also received from block 48 an assessment of whether or not there is interlaminar failure. The determination of whether there is damage or further damage in block 56 can be performed by either very simple or very complex algorithms depending upon, ultimately, the state of knowledge to mathematically describe the damage of failure thresholds. These algorithms may simply be the comparison of individual ply stress or strain components with the nominal allowables. Varying degrees of complexity may be included, accumulating in algorithms containing functional dependents on complete stress and strain states, prior damage states, statistical distributions of failure surfaces, and both partial and temporal derivatives of stress and strain states. The degradation of a ply, and ultimately the element stiffness may be handled through non-linear constitutive ply or smeared stiffness models that would capture the effects due to the damage. Ideally, this could be represented by the history state and behavior parameters that would be computed by damage algorithms and imply the current degrees of anisotropic "softness" to the master finite element calculation. If no damage is determined, the process returns to block 28 of FIG. 2. However, if failure has indeed been determined, new ply moduli are determined and the damage is recorded in block 58. It should be noted that block 58 is equivalent to blocks 24 and 26 of the FIG. 2 flow chart. Thereafter, the analysis is returned to the main flow chart of FIG. 2, and more particularly to block 30 thereof.

Return to the FIG. 2 illustration. It can be seen that if it has been determined that there is no failure per block 28, then the present invention method will proceed to either increment the load or increment the time in which the load is applied to the laminate per block 32. If no failure is assessed in the ply even with the incremental load or after the same load has been applied to the ply for a predetermined greater amount of time, then the analysis is determined to be finished for that particular ply. On the other hand, upon a determination that there is damage, per block 30, decision is made on whether the stiffness parameters of the ply have been changed. The decision from block 30 is intended to determine whether or not an interaction is required while block 34 specifically assesses whether or not the change is significant enough to warrant only a change in the element stiffness or allow the computation to proceed to the next load on time increment. Implications relating to changing damage state are also pertinent. If the change is significant, i.e., equals or exceeds a predetermined value, the element stiffness is reformulated in block 6. If it is insignificant, i.e., is less than a predetermined value, the change is further assessed in block 34. If the further assessment of the change is deemed to be insignificant, the analysis proceeds to block 32 as having been finished. If however the change is determined to be significant, the element stiffness parameters are reformulated per block 36. The evaluation of the ply can continue until a maximum load for the laminate member is determined.

Figure 5:
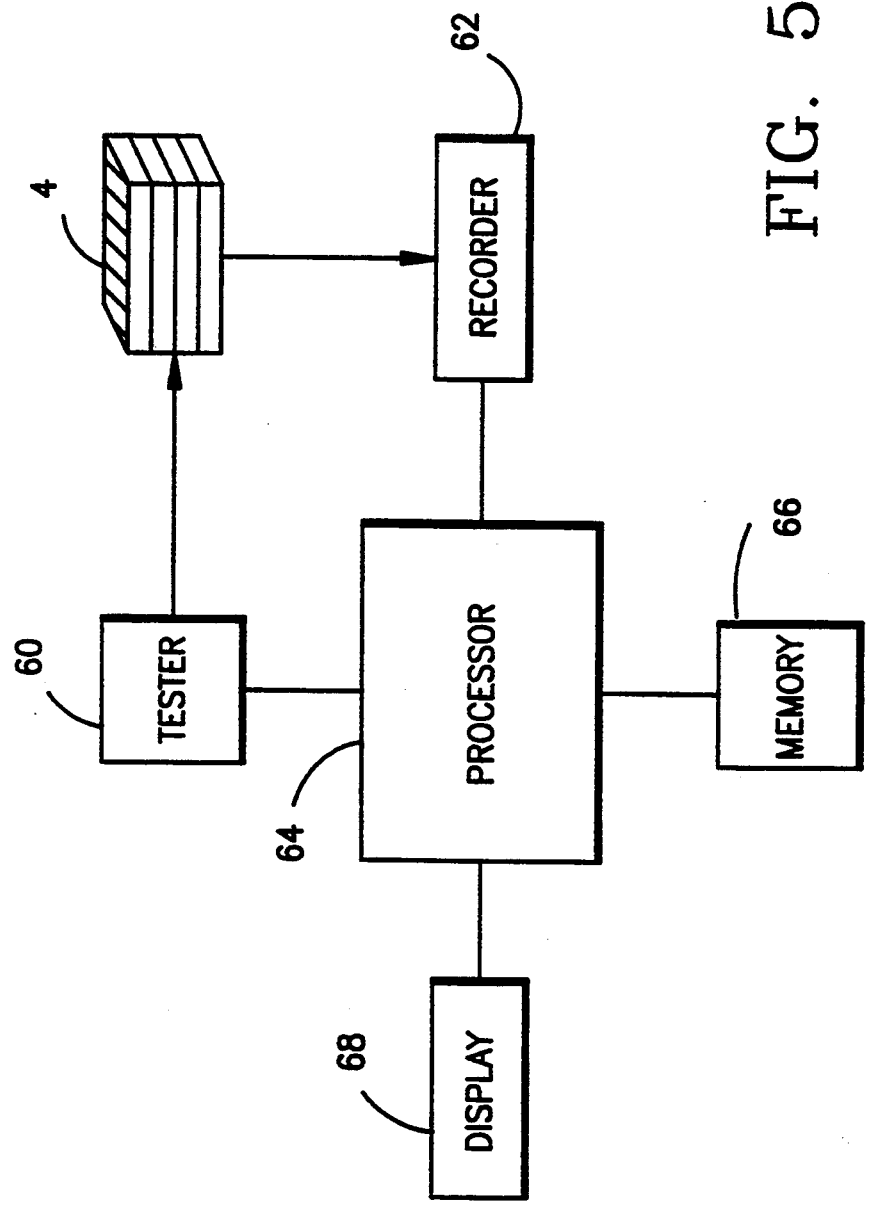
FIG. 5 is a simplified block diagram of the different components required for operating the present invention method.

The hardware components for performing the method of the present invention is illustrated in FIG. 5. As shown, a tester 60, such as a strain gauge or a micro measurement instrument, could be used to test and measure the strain and stress states of the different plies of laminate member 4. A recorder 62 such as a Niconet scope may be used to record the strain and stress states of the different plies of the laminate 4, as it is being tested. Tester 60 and recorder 62 are controlled by a processor 64, which may be a HP 730 workstation. A memory 66 is provided for storing any detected damage states. Of course, the stored data may be used to further determine the ply stiffness or any changes relating thereto, as discussed with respect to the flow chart of FIG. 3. Any result obtained can be displayed in graphical format to a user per display 68.

Inasmuch as the present invention is subject to many variations, modifications, and changes in detail, it is intended that all matter described throughout this specification and shown in the accompanying drawings be interpreted as illustrative and not in a limiting sense. Accordingly, it is intended that the invention be limited only by the spirit and scope of the appended claims.

We claim:

1. A method of analyzing the effects of progressive structural damage for a composite material member composed of multiple plies being subjected to loading forces, comprising the steps of:
    deducing stress and strain states of each of said plies of said member;
    applying predetermined failure criteria to said plies to determine if there is local failure in any of said plies; said step of applying predetermined failure criteria to said plies includes the step of assessing in-plane and interlaminar damage for each of said plies;
    upon determining no local failure in any of said plies, increasing either the amount of said loading forces or the time said loading forces are applied to said member until either a predetermined maximum load is reached for said member, local failure in any of said plies is detected or analyzing is finished; and upon determining local failure in any of said plies:
    computing new stiffness parameters for each of said plies where local failure is detected;
    storing damage information relating to any failed ply.

2. Method of claim 1, further comprising:
    determining a change between newly computed stiffness parameters and previously computed stiffness parameters for the region of each of said plies where failure was detected;
    reformulating the stiffness parameters for said region of each of said plies if the change is determined to equal or exceed a predetermined value.

3. Method of claim 1, wherein said applying failure criteria step further comprises the steps of:
    examining the stress and strain states of each of said plies to determine if each said ply is damage-free or has prior damage;
    computing new ply moduli for said each ply if damage results from any assessed failure;
    recording the damage as said damage information.

4. Method of claim 3, wherein said member comprises a laminate or layered multiple ply structure each of whose plies is made of continuous fibers in either a polymeric or metal matrix material, wherein if in-plane damage is assessed, said assessing step further comprises the steps of:
    evaluating the fiber and matrix of said each ply; and
    wherein said applying failure criteria step further comprises the step of:
        determining if any of the assessed in-plane and interlaminar failures result in damage to said each ply.

5. Method of claim 3, wherein said member comprises a laminate or layered multiple ply structure each of whose plies is made of long, discontinuous but preferentially oriented fibers in either a polymeric or metal matrix material, wherein if in-plane damage is assessed, said assessing step further comprises the steps of:
    evaluating the fiber and matrix of said each ply; and
    wherein said applying failure criteria step further comprises the step of:
        determining if any of the assessed in-plane and interlaminar failures result in damage to said each ply.

6. Method of claim 3, wherein said assessing step further comprising the step of:
    projecting an onset of damage from ply level estimates of said stress and strain states.

7. Method of claim 3, wherein said assessing step further comprising the step of:
    projecting an onset of damage from global estimates of said stress and strain states.

8. Method of claim 3, wherein once damage has been assessed, further comprising the steps of:
    calculating stress and strain states of each of said plies region by region;
    evaluating and estimating the damage for each said ply;
    computing new stiffness parameters for each damaged ply;
    storing information relating to said evaluated and estimated damage;
    reformulating the stiffness parameters for each region of each said ply evaluated as being damaged;
    specifying a next increase of the loading forces;
    recalculating stress and strain states of each said ply region by region.

9. Method of claim 4, further comprising the step of:
    defining a statistical distribution of the mechanical properties of said each ply by also assessing the tensile, compressive, shear, and/or coupled local deformation of said each ply.

10. Method of claim 1, further comprising the steps of:
    normalizing the stress and strain states of each of said plies; and
    displaying said stress and strain states graphically.

11. Method of claim 4, further comprising the step of:
    displaying any damage of said structure in graphically.

* * * * *